United States Patent
Hancox et al.

(10) Patent No.: US 9,763,950 B2
(45) Date of Patent: Sep. 19, 2017

(54) COMBINATION TREATMENT (71) Applicant: AstraZeneca AB, Sodertalje (SE)

(72) Inventors: Ursula Joy Hancox, Macclesfield (GB); Sabina Cosulich, Macclesfield (GB); Barry Robert Davies, Macclesfield (GB)

(73) Assignee: ASTRAZENECA AB (SE)

( * ) Notice: Subject to any disclaimer, the term of this patent is extended or adjusted under 35 U.S.C. 154(b) by 0 days.

(21) Appl. No.: 14/772,472

(22) PCT Filed: Mar. 3, 2014

(86) PCT No.: PCT/GB2014/050618
§ 371 (c)(1),
(2) Date: Sep. 3, 2015

(87) PCT Pub. No.: WO2014/135851
PCT Pub. Date: Sep. 12, 2014

(65) Prior Publication Data
US 2016/0022690 A1 Jan. 28, 2016

Related U.S. Application Data (60) Provisional application No. 61/771,974, filed on Mar. 4, 2013, provisional application No. 61/772,079, filed on Mar. 4, 2013.

(51) Int. Cl.
*A61K 31/54* (2006.01)
*A61K 31/535* (2006.01)
*A61K 31/5377* (2006.01)
*A61K 31/337* (2006.01)

(52) U.S. Cl.
CPC ........ *A61K 31/5377* (2013.01); *A61K 31/337* (2013.01)

(58) Field of Classification Search
CPC .............. A61K 2300/00; A61K 31/337; A61K 31/5377
USPC ...................................................... 514/233.5
See application file for complete search history.

(56) References Cited

U.S. PATENT DOCUMENTS

| | | | |
|---|---|---|---|
| 5,439,686 A | 8/1995 | Desai et al. | |
| 6,645,528 B1 | 11/2003 | Straub et al. | |
| 6,749,868 B1 | 6/2004 | Desai et al. | |
| 8,399,460 B2 * | 3/2013 | Barlaam | C07D 311/22 514/233.5 |
| 8,673,906 B2 * | 3/2014 | Barlaam | C07D 311/22 514/233.5 |
| 9,029,374 B2 * | 5/2015 | Barlaam | C07D 311/22 514/233.5 |
| 2007/0082838 A1 | 4/2007 | De et al. | |
| 2007/0117744 A1 | 5/2007 | Desai et al. | |
| 2008/0161382 A1 | 7/2008 | Desai et al. | |
| 2011/0098271 A1 * | 4/2011 | Barlaam | C07D 311/22 514/210.18 |
| 2016/0060240 A1 | 3/2016 | Barlaam et al. | |
| 2016/0272607 A1 | 9/2016 | Barlaam et al. | |

FOREIGN PATENT DOCUMENTS

| | | |
|---|---|---|
| WO | 9006921 A1 | 6/1990 |
| WO | 2004016607 A1 | 2/2004 |
| WO | 2005056014 A1 | 6/2005 |
| WO | 2008064244 A2 | 5/2008 |
| WO | 2011051704 A1 | 5/2011 |
| WO | 2012131399 A1 | 10/2012 |

OTHER PUBLICATIONS

Abid et al; 'Vascular Endothelial Growth Factor Activates PI3K/Akt/Forkhead Signaling in Endothelial Cells'; Arterioscler. Thromb. Vasc. Biol.; 2004, 24, 294-300.
Abrams et al; 'Enhancing therapeutic efficacy by targeting nononcogene addicted cells with combinations of signal transduction inhibitors and chemotherapy'; Cell Cycle, 2010, 9:9, 1839-1846.
Bender, A. et al; 'PI3K inhibitors prime neuroblastoma cells for chemotherapy by shifting the balance towards pro-apoptotic Bcl-2 proteins and enhanced mitochondrial apoptosis'; Oncogene. published online Sep. 20, 2010, vol. 30, No. 4, pp. 494-503.
Blume-Jensen et al; 'Oncogenic kinase signalling'; Nature; 2001; vol. 411; pp. 355-365.
Bradley MO et al; 'Tumor targeting by covalent conjugation of a natural fatty acid to paclitaxel'; Clin. Cancer Res. Oct. 2001; vol. 7, pp. 3229-3238.
Bradshaw, 'Cell transformation: the role of oncogenes and growth factors', Mutagenesis, 1986, vol. 1, No. 2., pp. 91-97.
Chen et al; 'Characterization of structurally distinct, isoform-selective phosphoinositide 3'-kinase inhibitors in combination with radiation I the treatment of glioblastoma'; Molecular Cancer Therapeutics; 2008; vol. 7; pp. 841-850.
Coussens et al, 'Inflammation and cancer'; Nature, 2002, vol. 420, pp. 860-867.
Foster et al; 'The phosphoinositide (PI) 3-kinase family'; J. Cell Science, 2003, 116: pp. 3037-3040.
Harari et al; 'Molecular mechanisms underlying ErbB2/HER2 action in breast cancer'; Oncogene, 2000, 19, pp. 6102-6114.
Herman et al; 'Phosphatidylinositol 3-kinase-d inhibitor CAL-101 shows promising preclinical activity in chronic lymphocytic leukemia by antagonizing intrinsic and extrinsic cellular survival signals'; Blood, Sep. 23, 2010, vol. 116, No. 12, pp. 2078-2088.

(Continued)

*Primary Examiner* — My-Chau T Tran
(74) *Attorney, Agent, or Firm* — Meaghan L. Richmond (57) ABSTRACT

The present invention relates to the use of combinations comprising 8-[(1R)-1-(3,5-difluorophenylamino)ethyl]-N,N-dimethyl-2-morpholino-4-oxo-4H-chromene-6-carboxamide or a pharmaceutically acceptable salt thereof and a taxane in the treatment or prophylaxis of cancer; pharmaceutical compositions comprising Compound [I] (or a pharmaceutically acceptable salt thereof) and a taxane; kits comprising Compound [I] or a pharmaceutically acceptable salt thereof and a taxane, optionally with instructions for use; and methods of treatment comprising the simultaneous, sequential or separate administration of Compound [I] or a pharmaceutically acceptable salt thereof and a taxane to warm-blooded animal, such as man.

13 Claims, 4 Drawing Sheets

(56) References Cited

OTHER PUBLICATIONS

Hoellenriegel et al; 'The phosphoinositide 3'-kinase delta inhibitor, CAL-101, inhibits B-cell receptor signaling and chemokine networks in chronic lymphocytic leukemia'; Blood, Sep. 29, 2011, vol. 118, No. 13, pp. 3603-3612.
Fan et al; 'A dual PI3 kinase/mTOR inhibitor reveals emergent efficacy in glioma'; Cancer Cell; May 2006; vol. 9; pp. 341-349.
Ikeda et al; 'PI3K/p110d is a novel therapeutic target in multiple myeloma';Blood, Sep. 2, 2010, vol. 116, No. 9, pp. 1460-1468.
Katso et al; 'Cellular function of phosphoinositide 3-kinases: Implications for Development, Immunity, Homeostasis, and Cancer'; Annual Rev. Cell, Dev. Biol., 2001, vol. 17; pp. 615-617.
Kauffmann-Zeh et al; 'Suppression of c-Myc-induced apoptosis by Ras signalling through PI(3)K and PKB'; Nature, Feb. 6, 1997, vol. 385, pp. 544-548.
Koyasu; 'The role of PI3K in immune cells'; Nature Immunology, Apr. 2003, vol. 4, pp. 313-319.
Lannutti et al; 'CAL-101, a p110d selective phosphatidylinositol-3-kinase inhibitor for the treatment of B-cell malignancies, inhibits PI3K signaling and cellular viability'; Blood, 2011, 117, 591-594.
Larson et al; 'New Approaches to Anti-Tumor Therapy'; Ann. Reports in Med. Chem., 1989, Chpt. 13, pp. 121-128.
Li; 'Poly(L-glutamic acid)—anticancer drug conjugates'; Adv. Drug Deliv. Rev; 2002; vol. 54, pp. 695-713.
Ma et al; 'PIK3CA as an oncogene in cervical cancer'; Oncogene, 2000, vol. 19: pp. 2739-2744.
Nicholson et al; 'The protein kinase B/Akt signalling pathway in human malignancy'; Cellular Signalling, 2002, vol. 14, pp. 381-395.
Philp et al; 'The Phosphatidylinositol 3'-kinase p85α Gene Is an Oncogene in Human Ovarian and Colon Tumors'; Cancer Research, 2001, vol. 61, pp. 7426-7429.
Prasad et al; 'Role of Phosphoinositide 3-Kinase in Cardiac Function and Heart Failure'; Trends in Cardiovascular Medicine, 2003, vol. 13, No. 5, pp. 206-212.
Samuels et al; 'High Frequency of Mutations of the PIK3CA Gene in Human Cancers'; Science, Apr. 23, 2004, vol. 304, p. 554.
Sawyer; 'Cancer Metastasis Therapeutic Targets and Drug Discovery: Emerging Small-Molecule Protein Kinase Inhibitors'; Expert Opinion Investig. Drugs, 2004, vol. 13, pp. 1-19.
Shayesteh et al; 'PIK3CA is implicated as an oncogene in ovarian cancer'; Nature Genetics, Jan. 1999, vol. 21: pp. 99-102.
Simpson et al.; 'PTEN: Life as a Tumor Suppressor'; Exp. Cell Res., 2001, vol. 264, pp. 29-41.
Torbett et al; 'A chemical screen in diverse breast cancer cell lines reveals genetic enhancers and suppressors of sensitivity to PI3K isoform-selective inhibition'; Biochemical Journal; 2008; vol. 415; pp. 97-110.
Vanhaesebroeck et al; 'Phosphoinositide 3-kinases: a conserved family of signal transducers'; Trends in Biol. Sci., 1997, vol. 22, pp. 267-272.
Vara et al; 'PI3K/Akt signalling pathway and cancer; Cancer Treatment Reviews', 2004, vol. 30, pp. 193-204.
Vivanco et al.; The Phosphatidylinositol 3-kinase-AKT Pathway in Human Cancer; Nature Reviews Cancer, Jul. 2002, vol. 2, pp. 489-501.
Wallin et al; 'GDC-0941, a novel class I selective PI3K inhibitor, enhances the efficacy of docetaxel in human breast cancer models by increasing cell death in vitro and in vivo'; Clinical Cancer Research, 2012, vol. 18, pp. 3901-3911.
Wilks; Protein Tyrosine Kinase Growth Factor Receptors and their Ligands in Development Differentiation, and Cancer; Advances in Cancer Research, 1993, 60, 43-73.
Wymann et al; 'Phosphoinositide 3-kinase signalling—which way to target?'; Trends in Pharmacological Science, Jul. 2003, vol. 24, No. 7, pp. 366-376.
Yarden et al; 'Growth Factor Receptor Tyrosine Kinases'; Ann. Rev. Biochem., 1988, 57, pp. 443-478.
Hancox et al., "AZD8186: a potent selective inhibitor of PI3K beta targeting PTEN-deficieint tumours dependent on dysregulated PI3K beta signalling", Cancer Research, vol. 73, No. 8, Suppl. 1, Apr. 2013, p. 3264, XP002723318 & 104th Annual Meeting of the American Association for Cancer Research (AACR), Washington DC, USA, Apr. 6-10, 2013, Poster Presentation.

* cited by examiner

COMBINATION TREATMENT

RELATED APPLICATIONS

This application is a National Stage application under 35 U.S.C. §371 of International Application No. PCT/GB2014/050618, filed Mar. 3, 2014, which claims the benefit of priority to U.S. Provisional Patent Application No. 61/771,974, filed Mar. 4, 2013 and U.S. Provisional Patent Application No. 61/772,079, filed Mar. 4, 2013.

The present invention relates to the use of combinations comprising 8-[(1R)-1-(3,5-difluorophenylamino)ethyl]-N,N-dimethyl-2-morpholino-4-oxo-4H-chromene-6-carboxamide (hereafter "Compound [I]") or a pharmaceutically acceptable salt thereof and a taxane in the treatment or prophylaxis of cancer. Taxanes include established cancer drugs such as docetaxel (Taxotere™) and paclitaxel (Taxol™). Other taxanes include cabazitaxel, larotaxel, ortataxel, and tesetaxel. The invention also relates to pharmaceutical compositions comprising Compound [I] or a pharmaceutically acceptable salt thereof and a taxane; and to kits comprising Compound [I] or a pharmaceutically acceptable salt thereof and a taxane, optionally with instructions for use. The invention further relates to methods of treatment comprising the simultaneous, sequential or separate administration of Compound [I] or a pharmaceutically acceptable salt thereof and a taxane to warm-blooded animal, such as man.

It has been discovered that a cell may become cancerous by virtue of the transformation of a portion of its DNA into an oncogene, a gene which, on activation, leads to the formation of malignant tumour cells (Bradshaw, *Mutagenesis*, 1986, 1, 91). Several such oncogenes give rise to the production of peptides, which are receptors for growth factors. Activation of the growth factor receptor complex subsequently leads to an increase in cell proliferation. It is known, for example, that several oncogenes encode tyrosine kinase enzymes and that certain growth factors receptors are also tyrosine kinase enzymes (Yarden et al., *Ann. Rev. Biochem.*, 1988, 57, 443; Larsen et al., *Ann. Reports in Med. Chem.*, 1989, Chpt. 13). The first group of tyrosine kinases to be identified arose from viral oncogenes, for example pp60$^{v\text{-}Src}$ tyrosine kinase (otherwise known as v-Src), and the corresponding tyrosine kinases in normal cells, for example pp60$^{c\text{-}Src}$ tyrosine kinase (otherwise known as c-Src).

Receptor tyrosine kinases are important in the transmission of biochemical signals which initiate cell replication. They are large enzymes which span the cell membrane and possess an extracellular binding domain for growth factors such as epidermal growth factor (EGF) and an intracellular portion which functions as a kinase to phosphorylate tyrosine amino acids in proteins and hence to influence cell proliferation. Various classes of receptor tyrosine kinases are known (Wilks, *Advances in Cancer Research*, 1993, 60, 43-73) including lipid kinases, which are located intracellularly and are involved in the transmission of biochemical signals such as those that influence tumour cell growth and invasiveness. Various classes of lipid kinases are known including the PI 3-kinase family, which is alternatively known as the phosphatidylinositol-3-kinase family.

It is now well understood that deregulation of oncogenes and tumour-suppressor genes contributes to the formation of malignant tumours, for example by way of increased cell proliferation or increased cell survival. It is also now known that signalling pathways mediated by the PI 3-kinase family have a central role in a number of cell processes including proliferation and survival, and deregulation of these pathways is a causative factor a wide spectrum of human cancers and other diseases (Katso et al., *Annual Rev. Cell Dev. Biol.*, 2001, 17: 615-617 and Foster et al., *J. Cell Science*, 2003, 116: 3037-3040).

The PI 3-kinase family of lipid kinases is a group of enzymes that phosphorylate the 3-position of the inositol ring of phosphatidylinositol (PI). Three major groups of PI 3-kinase enzymes are known which are classified according to their physiological substrate specificity (Vanhaesebroeck et al., *Trends in Biol. Sci.*, 1997, 22, 267). Class III PI 3-kinase enzymes phosphorylate PI alone. In contrast, Class II PI 3-kinase enzymes phosphorylate both PI and PI 4-phosphate [abbreviated hereinafter to PI(4)P]. Class I PI 3-kinase enzymes phosphorylate PI, PI(4)P and PI 4,5-bisphosphate [abbreviated hereinafter to PI(4,5)P2], although only PI(4,5)P2 is believed to be the physiological cellular substrate. Phosphorylation of PI(4,5)P2 produces the lipid second messenger PI 3,4,5-triphosphate [abbreviated hereinafter to PI(3,4,5)P3]. More distantly related members of this superfamily are Class IV kinases such as mTOR and DNA-dependent kinase that phosphorylate serine/threonine residues within protein substrates. The most studied and understood of these lipid kinases are the Class I PI 3-kinase enzymes.

Class I PI 3-kinase is a heterodimer consisting of a p110 catalytic subunit and a regulatory subunit, and the family is further divided into Class Ia and Class Ib enzymes on the basis of regulatory partners and mechanism of regulation. Class Ia enzymes, include PI 3-kinase β, and consist of three distinct catalytic subunits (p110, p110β and p110δ) that dimerise with five distinct regulatory subunits (p85α, p55α, p50α, p85β and p55γ), with all catalytic subunits being able to interact with all regulatory subunits to form a variety of heterodimers. Class Ia PI 3-kinase enzymes are generally activated in response to growth factor-stimulation of receptor tyrosine kinases, via interaction of the regulatory subunit SH2 domains with specific phospho-tyrosine residues of the activated receptor or adaptor proteins such as IRS-1. Both p110α and p110β are constitutively expressed in all cell types, whereas p110δ expression is more restricted to leukocyte populations and some epithelial cells. In contrast, the single Class Ib enzyme consists of a p110γ catalytic subunit that interacts with a p101 regulatory subunit. Furthermore, the Class Ib enzymes are activated in response to G-protein coupled receptor (GPCR) systems as well as by the mechanisms described above.

There is now considerable evidence indicating that Class Ia PI 3-kinase enzymes, which include PI 3-kinase β, contribute to tumourigenesis in a wide variety of human cancers, either directly or indirectly (Vivanco and Sawyers, *Nature Reviews Cancer*, 2002, 2, 489-501). For example, the p110α subunit is amplified in some tumours such as those of the ovary (Shayesteh et al., *Nature Genetics*, 1999, 21: 99-102) and cervix (Ma et al., *Oncogene*, 2000, 19: 2739-2744). Activating mutations within the catalytic site of p110α have been associated with various other tumours such as those of the colorectal region and of the breast and lung (Samuels et al., *Science*, 2004, 304, 554). Tumour-related mutations in p85α have also been identified in cancers such as those of the ovary and colon (Philp et al., *Cancer Research*, 2001, 61, 7426-7429). PI 3 kinase-β plays a critical role in B-cell function and has been shown to be a mediator of survival signalling in a range of B-cell malignancies. This includes, but may not be limited to, chronic lymphocytic leukaemia (CLL), acute lymphoblastic leukaemia (ALL), follicular lymphoma, diffuse large B-cell lymphoma (DLBCL) and mantle cell lymphoma (Ikeda et al., *Blood*, 2010, 116, 1460-1468; Herman et al., *Blood*, 2010, 116, 2078-2088; Lannutti et al., *Blood*, 2011, 117, 591-594; Hoellenriegel et al., *Blood*, 2011, 118, 3603-3612). In addition to direct effects, it is believed that activation of Class Ia PI 3-kinase contributes to tumourigenic events that occur upstream in signalling pathways, for example by way of ligand-dependent or ligand-independent activation of receptor tyrosine kinases, GPCR systems or integrins (Vara et al., *Cancer Treatment Reviews*, 2004, 30, 193-204). Examples of such upstream signalling pathways include over-expression of the receptor tyrosine kinase Erb2 in a variety of tumours leading to activation of PI 3-kinase-mediated pathways (Haran et al., *Oncogene*, 2000, 19, 6102-6114) and over-expression of the oncogene Ras (Kauffmann-Zeh et al., *Nature*, 1997, 385, 544-548). In addition, Class Ia PI 3-kinases may contribute indirectly to tumourigenesis caused by various downstream signalling events. For example, loss of the effect of the PTEN tumour-suppressor phosphatase that catalyses conversion of PI(3,4,5)P3 back to PI(4,5)P2 is associated with a very broad range of tumours via deregulation of PI 3-kinase-mediated production of PI(3,4,5)P3 (Simpson and Parsons, *Exp. Cell Res.*, 2001, 264, 29-41). Furthermore, augmentation of the effects of other PI 3-kinase-mediated signalling events is believed to contribute to a variety of cancers, for example by activation of AKT (Nicholson and Anderson, *Cellular Signalling*, 2002, 14, 381-395).

In addition to a role in mediating proliferative and survival signalling in tumour cells, there is also good evidence that Class Ia PI 3-kinase enzymes will also contribute to tumourigenesis via its function in tumour-associated stromal cells. For example, PI 3-kinase signalling is known to play an important role in mediating angiogenic events in endothelial cells in response to pro-angiogenic factors such as VEGF (Abid et al., *Arterioscler. Thromb. Vasc. Biol.*, 2004, 24, 294-300). As Class I PI 3-kinase enzymes are also involved in motility and migration (Sawyer, *Expert Opinion Investig. Drugs*, 2004, 13, 1-19), PI 3-kinase inhibitors should provide therapeutic benefit via inhibition of tumour cell invasion and metastasis.

In addition, Class I PI 3-kinase enzymes play an important role in the regulation of immune cells with PI 3-kinase activity contributing to pro-tumourigenic effects of inflammatory cells (Coussens and Werb, *Nature*, 2002, 420, 860-867).

These findings suggest that pharmacological inhibitors of Class I PI 3-kinase enzymes should be of therapeutic value for treatment of the various forms of the disease of cancer comprising solid tumours such as carcinomas and sarcomas and the leukaemias and lymphoid malignancies. In particular, inhibitors of Class I PI 3-kinase enzymes should be of therapeutic value for treatment of, for example, cancer of the breast, colorectum, lung (including small cell lung cancer, non-small cell lung cancer and bronchioalveolar cancer) and prostate, and of cancer of the bile duct, bone, bladder, brain, head and neck, kidney, liver, gastrointestinal tissue, oesophagus, ovary, pancreas, skin, testes, thyroid, uterus, cervix and vulva, and of leukaemias (including acute lymphoblastic leukaemia, Chronic Lymphocytic Leukaemia and chronic myelogenous leukaemia), multiple myeloma and lymphomas (including non-Hodgkin's lymphomas such as diffuse large B-cell lymphoma, follicular lymphoma, and mantle cell lymphoma).

Generally, investigators have explored the physiological and pathological roles of the PI 3-kinase enzyme family using the aforementioned PI 3-kinase inhibitors LY294002 and wortmannin. Although use of those compounds may suggest a role for PI 3-kinase in a cellular event, they are not sufficiently selective within the PI 3-kinase family to allow dissection of the individual roles of the family members. For this reason, more potent and selective pharmaceutical PI 3-kinase inhibitors would be useful to allow a more complete understanding of PI 3-kinase function and to provide useful therapeutic agents.

In addition to tumourigenesis, there is evidence that Class I PI 3-kinase enzymes play a role in other diseases (Wymann et al., *Trends in Pharmacological Science*, 2003, 24, 366-376). Both Class Ia PI 3-kinase enzymes and the single Class Ib enzyme have important roles in cells of the immune system (Koyasu, *Nature Immunology*, 2003, 4, 313-319) and thus they are therapeutic targets for inflammatory and allergic indications. Inhibition of PI 3-kinase is also, as described earlier, useful to treat cardiovascular disease via anti-inflammatory effects or directly by affecting cardiac myocytes (Prasad et al., *Trends in Cardiovascular Medicine*, 2003, 13, 206-212). Inhibition of PI 3-kinase is also useful to treat thrombosis. WO2004016607 provides a method of disrupting platelet aggregation and adhesion occurring under high shear conditions, and a method for inhibiting platelet activation induced by shear, where both methods comprise the administration of a selective PI 3-kinase β inhibitor. WO2004016607 also provides an antithrombotic method comprising administering an effective amount of a selective PI 3-kinase β inhibitor. According to the method, specific inhibition of thrombosis can be obtained without affecting normal haemostasis by targeting PI 3-kinase β that is important for shear-induced platelet activation. Said antithrombotic method therefore does not involve side effects caused by disruption of normal haemostasis, such as extending of bleeding time.

Compound [I] is a selective inhibitor of phosphoinositide (PI) 3-kinase β which is disclosed amongst many other Examples in international patent application publication number WO2011/051704. Compound [I] has the following structure:

Compound [I]

In WO2011/051704 it is stated that the compounds disclosed therein "may be applied as a sole therapy or may involve, in addition to the compound of the invention, conventional surgery or radiotherapy or chemotherapy". WO2011/051704 then lists many potential anti-tumour agents for use in such chemotherapy.

It has now been found that the use of Compound [I] in combination with a taxane surprisingly provides a synergistic effect, and may therefore provide an improved method of treating cancer compared to the use of either Compound [I] or a taxane alone.

A combination treatment may be considered to provide a synergistic effect if the effect is therapeutically superior, as measured by, for example, the extent of the response, the response rate, the time to disease progression or the survival period, to that achievable on dosing one or other of the components of the combination treatment at their conventional dose. For example, the effect of the combination treatment is synergistic if the use of the combination is superior to the effect achievable with Compound [I] or one of the specified combination partners, when used alone. In particular, the effect of the combination treatment is synergistic if efficacy can be maintained during combination treatment at a lower dose of one or more of the combination partners than is required for the corresponding monotherapy treatment. Further, the effect of the combination treatment is synergistic if a beneficial effect is obtained in a group of patients that does not respond (or responds poorly) to Compound [I] or one of the specified combination partners, when used alone.

A combination treatment may also be considered to provide a synergistic effect if one or both of the components may be dosed less frequently than the dosing schedule used for conventional dosing of each component when used alone, while not adversely impacting the beneficial effect otherwise achieved by the use of conventional amounts of an agent used alone. In particular, synergy is deemed to be present if the frequency of dosing of Compound [I] and/or a specified combination partner may be reduced relative to what would otherwise be conventional/required when using one of the combination partners alone, without detriment to one or more factors such as: extent of the response, the response rate, the time to disease progression and survival data and in particular without detriment to the duration of the response. Decreasing the dosing amount and frequency for a particular compound can lead to fewer and/or less troublesome side-effects than those that occur when conventional scheduling/doses are used.

In a first aspect of the invention there is provided a combination comprising Compound [I] or a pharmaceutically acceptable salt thereof and a taxane, for use in the treatment of cancer.

A pharmaceutically acceptable salt is, for example, an acid-addition salt with an inorganic or organic acid, for example hydrochloric acid, hydrobromic acid, methanesulphonic acid, sulphuric acid or trifluoroacetic acid.

Herein where the term "taxane" is used it is to be understood that this may refer to any chemical analogue which exerts its anticancer effect by stabilization of the tubulin microtubules involved in cell division.

Examples of taxanes that may be combined with Compound [I] include: (2aR,3aR,4aR,6R,9S,11S,12S,12aR,12bS)-6,12b-diacetoxy-9-[3(S)-(tert-butoxycarbonylamino)-2(R)-hydroxy-3-phenylpropionyloxy]-12-benzoyloxy-11-hydroxy-8,13,13-trimethyl-2a,3,3a,4,5,6,9,10,11,12,12a,12b-dodecahydro-1H-7,11-methanocyclodeca[3,4]-cyclopropa[4,5]benz[1,2-b]oxet-5-one dihydrate; paclitaxel (Taxol), BMS-184476 (7-methylthiomethylpaclitaxel); BMS-188797; BMS-275183; BMS-188797; BMS-109881; CYC-3204 (a penetratin-paclitaxel conjugate); Taxoprexin; DJ-927; Docetaxel (Taxotere™); Larotexel (XRP9881; RPR-109881A); XRP6258 (RPR112658); Milataxel (MAC-321); MST 997; MBT-206; NBT-287; Ortataxel; Protax-3; PG-TXL; PNU-166945; PNU-106258; Orataxel (BAY 59-8862; IDN 5109; semisynthetic taxane); TPI-287; Protaxel and MAC-321 (Taxalog).

Examples of formulations for taxanes include:

Conventional formulations of paclitaxel or docetaxel, for example the currently approved Taxol™ and Taxotere™ formulations;

Formulations with biocompatible polymers, particularly proteins such as albumin, more particularly nano-particle or micro-particle formulations of paclitaxel or docetaxel with albumin, for example Abraxane™ (described in U.S. Pat. No. 5,439,686 and U.S. Pat. No. 6,749,868) or NAB-docetaxel (described in, for example US 20080161382, US20070117744 and US 20070082838);

Polymer conjugates, particularly polymer conjugates of paclitaxel or docetaxel, more particularly conjugates of docetaxel or paclitaxel with poly-L-glutamate, for example Opaxio (also known as Xyotax, paclitaxel poliglumex, CT-2103 and described in for example Li C.; Poly (L-glutamic acid)—anticancer drug conjugates; Adv. Drug Deliv. Rev. 2002; 54: 695-713);

Conjugates of docetaxel or paclitaxel with a fatty acid, particularly conjugates of paclitaxel or docetaxel with docosahexaenoic acid (DHA), for example, Taxoprexin (DHA-paclitaxel, described in for example Bradley M O et al. Tumor targeting by covalent conjugation of a natural fatty acid to paclitaxel; Clin. Cancer Res. 2001; 7: 3229-38);

Microparticle compositions such as the porous microparticle formulations described in U.S. Pat. No. 6,645,528, for example the microparticle formulation of paclitaxel AI-850, comprising paclitaxel nanoparticles in a porous, hydrophilic matrix, composed primarily of a sugar; and Emulsions of paclitaxel or docetaxel in vitamin E, for example Tocosol.

In one embodiment the taxane is selected from paclitaxel, docetaxel and Abraxane.

In one embodiment the taxane is selected from docetaxel and paclitaxel.

In one embodiment the taxane is paclitaxel.

In one embodiment the taxane is docetaxel.

In one embodiment the taxane is abraxane.

In one embodiment the taxane is cabazitaxel.

In one embodiment the taxane is selected from docetaxel, paclitaxel, cabazitaxel, larotexel, ortataxel and tesetaxel.

Herein, where the term "combination" is used it is to be understood that this may refer to simultaneous, separate or sequential administration of the components of the combination.

In one embodiment "combination" refers to simultaneous administration of the components of the combination.

In one embodiment "combination" refers to separate administration of the components of the combination.

In one embodiment "combination" refers to sequential administration of the components of the combination.

As shown hereinafter, there are benefits in combining Compound [I] with a taxane (such as docetaxel) in the PC3 and HCC70 xenograft models. Furthermore, as also shown herein intermittent dosage of Compound [I] in combination with a taxane (such as doectaxel) has similar effectiveness at regulating tumour size as continuous dosage of Compound [I] in combination with a taxane (such as docetaxel). In particular, intermittent dosage of Compound [I] following only a single dose of a taxane (such as docetaxel) has similar effectiveness at regulating tumour size as continuous dosage of Compound [I] in combination with a taxane (such as docetaxel).

Therefore, in one embodiment there is provided a combination comprising Compound [I] or a pharmaceutically acceptable salt thereof and a taxane for use in the treatment of cancer, wherein the Compound [I] or a pharmaceutically acceptable salt thereof is dosed intermittently.

In one embodiment the dosage cycle comprises the intermittent dosage of Compound [I] or a pharmaceutically acceptable salt thereof.

For the avoidance of doubt, intermittent dosage of Compound [I] or a pharmaceutically acceptable salt thereof means that in a given dosage cycle there will be one or more days (for example 1, 2, 3, 4, 5, 6 or 7 days) where no Compound [I] or a pharmaceutically acceptable salt thereof is administered.

It may be advantageous, within a given dosage cycle, to administer one specific component of the combination before the other, i.e. to dose sequentially.

Therefore, in one embodiment the dosage cycle comprises the sequential administration of the Compound [I] or a pharmaceutically acceptable salt thereof prior to the administration of the taxane (such as docetaxel).

In another embodiment the dosage cycle comprises the sequential administration of the taxane (such as docetaxel) prior to the administration of Compound [I] or a pharmaceutically acceptable salt thereof.

In one embodiment the dosage cycle involves only a single dose of the taxane (such as docetaxel).

In one embodiment the dosage cycle comprises the sequential administration of the taxane (such as docetaxel) only within the 2 days prior to the first administration of Compound [I] or a pharmaceutically acceptable salt thereof within a dosage cycle.

In one embodiment the dosage cycle comprises the sequential administration of the taxane (such as docetaxel) only within the 24 hours prior to the first administration of Compound [I] or a pharmaceutically acceptable salt thereof within a dosage cycle.

In one embodiment the dosage cycle comprises the sequential administration of the taxane (such as docetaxel) only within the 12 hours prior to the first administration of Compound [I] or a pharmaceutically acceptable salt thereof within a dosage cycle.

In one embodiment the dosage cycle comprises the sequential administration of the taxane (such as docetaxel) only within the 6 hours prior to the first administration of Compound [I] or a pharmaceutically acceptable salt thereof within a dosage cycle.

In one embodiment the dosage cycle comprises the sequential administration of the taxane (such as docetaxel) only within the 3 hours prior to the first administration of Compound [I] or a pharmaceutically acceptable salt thereof within a dosage cycle.

In one embodiment the dosage cycle comprises the sequential administration of the taxane (such as docetaxel) only within the 1.5 hours prior to the first administration of Compound [I] or a pharmaceutically acceptable salt thereof within a dosage cycle.

For the avoidance of doubt "within the x hours prior to the first administration of Compound" means any time up to x hours before the first dosing of Compound [I] or a pharmaceutically acceptable salt thereof within a given dosage cycle, and includes substantially simultaneous dosing of the taxane (such as docetaxel) with the first dosing of Compound [I] or a pharmaceutically acceptable salt thereof of a given dosage cycle.

In one embodiment the dosage cycle is from 8 to 29 days in length.

In one embodiment the dosage cycle is from 15 to 29 days in length.

In one embodiment the dosage cycle is from 15 to 22 days in length.

In one embodiment the dosage cycle is from 22 to 29 days in length.

In one embodiment the dosage cycle is from 8 to 22 days in length.

In one embodiment the dosage cycle is from 8 to 15 days in length.

In one embodiment the dosage cycle is 29 days in length.
In one embodiment the dosage cycle is 22 days in length.
In one embodiment the dosage cycle is 15 days in length.
In one embodiment the dosage cycle is 8 days in length.

In one embodiment the dosage cycle comprises Compound [I] or a pharmaceutically acceptable salt thereof being dosed for at least one period (for example 1, 2, or 3 periods) of 3-5 consecutive days (for example 3, 4 or 5 days), which period(s) are immediately followed by a further period of least one day (for example 2, 3, 4 or 5 consecutive days) where no Compound [I] or a pharmaceutically acceptable salt thereof is dosed.

In one embodiment the dosage cycle comprises at least one 7 day period, in which period Compound [I] or a pharmaceutically acceptable salt thereof is dosed only for 3-5 consecutive days.

In one embodiment the dosage cycle comprises one 7 day period in which Compound [I] or a pharmaceutically acceptable salt thereof is only dosed for 3-5 consecutive days.

In one embodiment the dosage cycle comprises two 7 day periods in which Compound [I] or a pharmaceutically acceptable salt thereof is only dosed for 3-5 consecutive days.

In one embodiment the dosage cycle comprises three 7 day periods in which Compound [I] or a pharmaceutically acceptable salt thereof is only dosed for 3-5 consecutive days.

In one embodiment the dosage cycle comprises Compound [I] or a pharmaceutically acceptable salt thereof being dosed for at least one period of 5 consecutive days immediately followed by a further period of 2 consecutive days where no Compound [I] or a pharmaceutically acceptable salt thereof is dosed.

In one embodiment the dosage cycle comprises Compound [I] or a pharmaceutically acceptable salt thereof being dosed for at least one period of 4 consecutive days immediately followed by a further period of 3 consecutive days where no Compound [I] or a pharmaceutically acceptable salt thereof is dosed.

In one embodiment the dosage cycle comprises Compound [I] or a pharmaceutically acceptable salt thereof being dosed for at least one period of 3 consecutive days immediately followed by a further period of 4 consecutive days where no Compound [I] or a pharmaceutically acceptable salt thereof is dosed.

In one embodiment the dosage cycle is 29 days long and comprises four 7 day periods, each such period consisting of 5 days where Compound [I] or a pharmaceutically acceptable salt thereof is dosed followed by 2 days where no Compound [I] or a pharmaceutically acceptable salt thereof is dosed.

In one embodiment the dosage cycle is 29 days long and comprises four 7 day periods, each such period consisting of 4 days where Compound [I] or a pharmaceutically acceptable salt thereof is dosed followed by 3 days where no Compound [I] or a pharmaceutically acceptable salt thereof is dosed.

In one embodiment the dosage cycle is 29 days long and comprises four 7 day periods, each such period consisting of 3 days where Compound [I] or a pharmaceutically acceptable salt thereof is dosed followed by 4 days where no Compound [I] or a pharmaceutically acceptable salt thereof is dosed.

In one embodiment the dosage cycle is 22 days long and comprises three 7 day periods, each such period consisting of 5 days where Compound [I] or a pharmaceutically acceptable salt thereof is dosed followed by 2 days where no Compound [I] or a pharmaceutically acceptable salt thereof is dosed.

In one embodiment the dosage cycle is 22 days long and comprises three 7 day periods, each such period consisting of 4 days where Compound [I] or a pharmaceutically acceptable salt thereof is dosed followed by 3 days where no Compound [I] or a pharmaceutically acceptable salt thereof is dosed.

In one embodiment the dosage cycle is 22 days long and comprises three 7 day periods, each such period consisting of 3 days where Compound [I] or a pharmaceutically acceptable salt thereof is dosed followed by 4 days where no Compound [I] or a pharmaceutically acceptable salt thereof is dosed.

In one embodiment the dosage cycle is 15 days long and comprises two 7 day periods, each such period consisting of 5 days where Compound [I] or a pharmaceutically acceptable salt thereof is dosed followed by 2 days where no Compound [I] or a pharmaceutically acceptable salt thereof is dosed.

In one embodiment the dosage cycle is 15 days long and comprises two 7 day periods, each such period consisting of 4 days where Compound [I] or a pharmaceutically acceptable salt thereof is dosed followed by 3 days where no Compound [I] or a pharmaceutically acceptable salt thereof is dosed.

In one embodiment the dosage cycle is 15 days long and comprises two 7 day periods, each such period consisting of 3 days where Compound [I] or a pharmaceutically acceptable salt thereof is dosed followed by 4 days where no Compound [I] or a pharmaceutically acceptable salt thereof is dosed.

In one embodiment the dosage cycle is 8 days long and comprises one 7 day period consisting of 5 days where Compound [I] or a pharmaceutically acceptable salt thereof is dosed followed by 2 days where no Compound [I] or a pharmaceutically acceptable salt thereof is dosed.

In one embodiment the dosage cycle is 8 days long and comprises one 7 day period consisting of 4 days where Compound [I] or a pharmaceutically acceptable salt thereof is dosed followed by 3 days where no Compound [I] or a pharmaceutically acceptable salt thereof is dosed.

In one embodiment the dosage cycle is 8 days long and comprises one 7 day period consisting of 3 days where Compound [I] or a pharmaceutically acceptable salt thereof is dosed followed by 4 days where no Compound [I] or a pharmaceutically acceptable salt thereof is dosed.

In one embodiment the dosage cycle is 8-29 days long and comprises a single administration of the taxane (such as docetaxel) within the 24 hours prior to the first administration of Compound [I] or a pharmaceutically acceptable salt thereof, followed by intermittent dosing of Compound [I] or a pharmaceutically acceptable salt thereof.

In one embodiment the dosage cycle is 15-29 days long and comprises the administration of the taxane (such as docetaxel) within the 24 hours prior to the first administration of Compound [I] or a pharmaceutically acceptable salt thereof, followed by intermittent dosing of Compound [I] or a pharmaceutically acceptable salt thereof in 7 day periods consisting of 5 days where Compound [I] or a pharmaceutically acceptable salt thereof is dosed followed by 2 days where no Compound [I] or a pharmaceutically acceptable salt thereof is dosed.

In one embodiment the dosage cycle is 15-29 days long and comprises the administration of the taxane (such as docetaxel) within the 24 hours prior to the first administration of Compound [I] or a pharmaceutically acceptable salt thereof, followed by intermittent dosing of Compound [I] or a pharmaceutically acceptable salt thereof in 7 day periods consisting of 4 days where Compound [I] or a pharmaceutically acceptable salt thereof is dosed followed by 3 days where no Compound [I] or a pharmaceutically acceptable salt thereof is dosed.

In one embodiment the dosage cycle is 15-29 days long and comprises the administration of the taxane (such as docetaxel) within the 24 hours prior to the first administration of Compound [I] or a pharmaceutically acceptable salt thereof, followed by intermittent dosing of Compound [I] or a pharmaceutically acceptable salt thereof in 7 day periods consisting of 3 days where Compound [I] or a pharmaceutically acceptable salt thereof is dosed followed by 4 days where no Compound [I] or a pharmaceutically acceptable salt thereof is dosed.

In one embodiment the dosage cycle comprises the following steps:
  a) Day 1: Administration of taxane (for example docetaxel);
  b) Days 2-6: Administration of Compound [I] or a pharmaceutically acceptable salt thereof;
  c) Days 7-8: No dosage of either Compound [I] or a pharmaceutically acceptable salt thereof or taxane;
  d) Days 9-13: Administration of Compound [I] or a pharmaceutically acceptable salt thereof;
  e) Days 14-15: No dosage of either Compound [I] or a pharmaceutically acceptable salt thereof or taxane;
  f) Days 16-20: Administration of Compound [I] or a pharmaceutically acceptable salt thereof;
  g) Days 21-22: No dosage of either Compound [I] or a pharmaceutically acceptable salt thereof or taxane.

In one embodiment the dosage cycle comprises the following steps:
  a) Day 1: Administration of taxane (for example docetaxel);
  b) Days 2-5: Administration of Compound [I] or a pharmaceutically acceptable salt thereof;
  c) Days 6-8: No dosage of either Compound [I] or a pharmaceutically acceptable salt thereof or taxane;
  d) Days 9-12: Administration of Compound [I] or a pharmaceutically acceptable salt thereof;
  e) Days 13-15: No dosage of either Compound [I] or a pharmaceutically acceptable salt thereof or taxane;
  f) Days 16-19: Administration of Compound [I] or a pharmaceutically acceptable salt thereof.
  g) Days 20-22: No dosage of either Compound [I] or a pharmaceutically acceptable salt thereof or taxane.

In one embodiment the dosage cycle comprises the following steps:

a) Day 1: Administration of taxane (for example docetaxel);
b) Days 2-4: Administration of Compound [I] or a pharmaceutically acceptable salt thereof;
c) Days 5-8: No dosage of either Compound [I] or a pharmaceutically acceptable salt thereof or taxane;
d) Days 9-11: Administration of Compound [I] or a pharmaceutically acceptable salt thereof;
e) Days 12-15: No dosage of either Compound [I] or a pharmaceutically acceptable salt thereof or taxane;
f) Days 16-18: Administration of Compound [I] or a pharmaceutically acceptable salt thereof.
g) Days 19-22: No dosage of either Compound [I] or a pharmaceutically acceptable salt thereof or taxane.

In one embodiment of the invention, Compound [I] or a pharmaceutically acceptable salt thereof is administered once daily on the days of a dosage cycle when it is dosed.

In one embodiment of the invention, Compound [I] or a pharmaceutically acceptable salt thereof is administered twice daily on the days of a dosage cycle when it is dosed.

For the avoidance of doubt, dosage cycles may be separated by a number of days (for example 1, 2, 3, 4, 5, 6 or 7 days) where none of the active combination components are administered.

In one aspect where Compound [I] is mentioned, the Compound [I] is 8-[(1R)-1-(3,5-difluorophenylamino)ethyl]-N,N-dimethyl-2-morpholino-4-oxo-4H-chromene-6-carboxamide.

In another aspect where Compound [I] is mentioned, the Compound [I] is a pharmaceutically acceptable salt of 8-[(1R)-1-(3,5-difluorophenylamino)ethyl]-N,N-dimethyl-2-morpholino-4-oxo-4H-chromene-6-carboxamide.

In one embodiment of the invention there is provided a combination comprising Compound [I] or a pharmaceutically acceptable salt thereof and docetaxel, for use in the treatment of cancer.

In one embodiment of the invention there is provided a combination comprising Compound [I] or a pharmaceutically acceptable salt thereof and docetaxel, for use in the treatment of cancer.

In one embodiment of the invention there is provided a combination comprising a pharmaceutically acceptable salt of Compound [I] and docetaxel, for use in the treatment of cancer.

According to a further aspect of the invention there is provided a pharmaceutical composition which comprises Compound [I] or a pharmaceutically acceptable salt thereof and a taxane in association with a pharmaceutically acceptable diluent or carrier.

According to a further aspect of the invention there is provided a pharmaceutical composition which comprises Compound [I] or a pharmaceutically acceptable salt thereof and docetaxel in association with a pharmaceutically acceptable diluent or carrier.

In one embodiment there is provided a pharmaceutical product comprising:
(i) a pharmaceutical composition which comprises Compound [I], or a pharmaceutically acceptable salt thereof, in association with a pharmaceutically acceptable diluent or carrier; and
(ii) a pharmaceutical composition which comprises a taxane, in association with a pharmaceutically acceptable diluent or carrier.

In one embodiment there is provided a pharmaceutical product comprising:
(i) a pharmaceutical composition which comprises Compound [I], or a pharmaceutically acceptable salt thereof, in association with a pharmaceutically acceptable diluent or carrier; and
(ii) a pharmaceutical composition which comprises docetaxel, in association with a pharmaceutically acceptable diluent or carrier.

In one aspect there is provided a method of treating cancer, in a warm-blooded animal, such as a human, which comprises administering to said animal an effective amount of Compound [I], or a pharmaceutically acceptable salt thereof, in combination with an effective amount of a taxane.

In one aspect there is provided a method of treating cancer, in a warm-blooded animal, such as a human, which comprises administering to said animal an effective amount of Compound [I], or a pharmaceutically acceptable salt thereof, in combination with an effective amount of docetaxel.

Where the treatment of cancer is indicated, it is to be understood that this may refer to the prevention of metastases and the treatment of metastases, i.e. cancer spread. Therefore the combination of the present invention might be used to treat a patient who has no metastases to stop them occurring, or to lengthen the time period before they occur, and to a patient who already has metastases to treat the metastases themselves. Furthermore the treatment of cancer may refer to treatment of an established primary tumour or tumours and developing primary tumour or tumours.

Therefore, in one aspect the treatment of cancer relates to the prevention of metastases.

In another aspect of the invention the treatment of cancer relates to the treatment of metastases.

In another aspect of the invention the treatment of cancer relates to treatment of an established primary tumour or tumours or developing primary tumour or tumours.

Herein, the treatment of cancer may refer to the prevention of cancer per se.

According to a further aspect of the invention, there is provided a kit comprising Compound [I], or a pharmaceutically acceptable salt thereof and a taxane, optionally with instructions for use.

According to a further aspect of the invention, there is provided a kit comprising Compound [I], or a pharmaceutically acceptable salt thereof and docetaxel, optionally with instructions for use.

According to a further aspect of the invention, there is provided a kit comprising:
a) Compound [I], or a pharmaceutically acceptable salt thereof, in a first unit dosage form;
b) a taxane, in a second unit dosage form;
c) container means for containing said first and second dosage forms; and optionally
d) instructions for use.

According to a further aspect of the invention, there is provided a kit comprising:
a) Compound [I], or a pharmaceutically acceptable salt thereof, in a first unit dosage form;
b) docetaxel, in a second unit dosage form;
c) container means for containing said first and second dosage forms; and optionally
d) instructions for use.

An example of a unit dosage form is a tablet for oral administration.

According to a further aspect of the invention there is provided a pharmaceutical composition which comprises Compound [I], or a pharmaceutically acceptable salt thereof;

and a taxane in association with a pharmaceutically acceptable diluent or carrier, for use in the treatment of cancer.

According to a further aspect of the invention there is provided a pharmaceutical composition which comprises Compound [I], or a pharmaceutically acceptable salt thereof; and docetaxel in association with a pharmaceutically acceptable diluent or carrier, for use in the treatment of cancer.

According to a further aspect of the invention there is provided a pharmaceutical composition which comprises Compound [I], or a pharmaceutically acceptable salt thereof, in association with a pharmaceutically acceptable diluent or carrier; in combination with a pharmaceutical composition which comprises a taxane, in association with a pharmaceutically acceptable diluent or carrier, for use in the treatment of cancer.

According to a further aspect of the invention there is provided a pharmaceutical composition which comprises Compound [I], or a pharmaceutically acceptable salt thereof, in association with a pharmaceutically acceptable diluent or carrier; in combination with a pharmaceutical composition which comprises docetaxel, in association with a pharmaceutically acceptable diluent or carrier, for use in the treatment of cancer.

The pharmaceutical compositions may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository. In general the above compositions may be prepared in a conventional manner using conventional excipients.

According to a further aspect of the present invention there is provided a kit comprising Compound [I], or a pharmaceutically acceptable salt thereof and a taxane; optionally with instructions for use; for use in the treatment of cancer.

According to a further aspect of the present invention there is provided a kit comprising Compound [I], or a pharmaceutically acceptable salt thereof and docetaxel; optionally with instructions for use; for use in the treatment of cancer.

According to a further aspect of the present invention there is provided a kit comprising:
a) Compound [I], or a pharmaceutically acceptable salt thereof, in a first unit dosage form;
b) a taxane;
c) container means for containing said first and second dosage forms; and optionally
d) instructions for use;
for use in the treatment of cancer.

According to a further aspect of the present invention there is provided a kit comprising:
a) Compound [I], or a pharmaceutically acceptable salt thereof, in a first unit dosage form;
b) docetaxel;
c) container means for containing said first and second dosage forms; and optionally
d) instructions for use;
for use in the treatment of cancer.

According to the present invention, there is provided a combination which comprises Compound [I], or a pharmaceutically acceptable salt thereof and a taxane for use as a medicament.

According to the present invention, there is provided a combination which comprises Compound [I], or a pharmaceutically acceptable salt thereof and docetaxel for use as a medicament.

According to another feature of the invention there is provided the use of Compound [I], or a pharmaceutically acceptable salt thereof, in combination with a taxane, in the manufacture of a medicament for the treatment of cancer.

According to another feature of the invention there is provided the use of Compound [I], or a pharmaceutically acceptable salt thereof, in combination with docetaxel, in the manufacture of a medicament for the treatment of cancer.

It may be convenient or medically appropriate for a physician to determine the exact dosage and scheduling for use of a combination product, such that the active components of the combination product may necessarily not be present together within a single dosage form at a fixed dose. Therefore a physician or pharmacist may prepare a combination medicament comprising the active combination products in readiness for simultaneous, separate or sequential combination use in medicine, for example to treat cancer in a warm-blooded animal, such as human.

According to another feature of the invention there is provided the use of Compound [I], or a pharmaceutically acceptable salt thereof, in combination with a taxane (such as docetaxel), in the preparation of a combination medicament for use in medicine.

According to another feature of the invention there is provided the use of Compound [I], or a pharmaceutically acceptable salt thereof, in combination with a taxane (such as docetaxel), in the preparation of a combination medicament for simultaneous, separate or sequential combination use in medicine.

According to another feature of the invention there is provided the use of Compound [I], or a pharmaceutically acceptable salt thereof, in combination with a taxane (such as docetaxel), in the preparation of a combination medicament for simultaneous, separate or sequential combination use for the treatment of cancer.

According to another feature of the invention there is provided the use of Compound [I], or a pharmaceutically acceptable salt thereof, in combination with a taxane (such as docetaxel), in the preparation of a combination medicament for simultaneous, separate or sequential combination use for the treatment of cancer in a warm-blooded animal such as a human.

According to another feature of the invention there is provided the use of Compound [I], or a pharmaceutically acceptable salt thereof, in combination with a taxane (such as docetaxel), in the preparation of a combination medicament for separate combination use for the treatment of cancer in a warm-blooded animal such as a human.

According to another feature of the invention there is provided the use of Compound [I], or a pharmaceutically acceptable salt thereof, in combination with a taxane (such as docetaxel), in the preparation of a combination medicament for sequential combination use for the treatment of cancer in a warm-blooded animal such as a human.

According to another feature of the invention there is provided the use of Compound [I], or a pharmaceutically acceptable salt thereof, in combination with a taxane (such as docetaxel), in the preparation of a combination medicament for the treatment of cancer.

According to a further aspect of the present invention there is provided a combination comprising Compound [I], or a pharmaceutically acceptable salt thereof, and a taxane (such as docetaxel), for use in the treatment of cancer.

In one embodiment there is provided Compound [I], or a pharmaceutically acceptable salt thereof, and a taxane (such as docetaxel) for use in the treatment of cancer in a warm-blooded animal such as a human.

In one embodiment there is provided Compound [I], or a pharmaceutically acceptable salt thereof, and a taxane (such as docetaxel), for use in the treatment of cancer in a warm-blooded animal such as a human; wherein the Compound [I], or a pharmaceutically acceptable salt thereof, and the taxane are administered simultaneously, separately or sequentially to the warm-blooded animal.

In one embodiment there is provided a method for the production of an anti-cancer effect in a warm-blooded animal such as a human, which comprises administering to said animal an effective amount of Compound [I] or a pharmaceutically acceptable salt thereof, optionally together with a pharmaceutically acceptable diluent or carrier; before, after or simultaneously with an effective amount of a taxane (such as docetaxel), optionally together with a pharmaceutically acceptable diluent or carrier.

Where cancer is referred to, it may refer to oesophageal cancer, myeloma, hepatocellular cancer, pancreatic cancer, cervical cancer, ewings tumour, neuroblastoma, kaposis sarcoma, ovarian cancer, breast cancer, colorectal cancer, prostate cancer, bladder cancer, melanoma, lung cancer—non small cell lung cancer, and small cell lung cancer, gastric cancer, head and neck cancer, brain cancer, renal cancer, lymphoma and leukaemia.

In one embodiment the cancer is prostate cancer.

In one embodiment the cancer is pancreatic cancer.

In one embodiment the cancer is castrate-resistant prostate cancer.

In one embodiment the cancer is small cell lung cancer.

In one embodiment the cancer is non-small cell lung cancer.

In one embodiment the cancer is squamous non-small cell lung cancer.

In one embodiment the cancer is colorectal cancer.

In one embodiment the cancer is ovarian cancer.

In one embodiment the cancer is breast cancer.

In one embodiment the cancer is triple negative breast cancer.

In one embodiment the cancer is prostate cancer, non-small cell lung cancer or breast cancer.

In one embodiment the cancer is castrate-resistant prostate cancer, squamous non-small cell lung cancer, colorectal cancer, pancreatic cancer or triple negative breast cancer.

In one embodiment the cancer is castrate-resistant prostate cancer, squamous non-small cell lung cancer or triple negative breast cancer.

In one embodiment the cancer is bladder cancer, oesophageal cancer, gastric cancer, melanoma, cervical cancer or renal cancer.

In one embodiment the cancer is endometrial, liver, stomach, thyroid, rectal or brain cancer.

In one embodiment the cancer is cancer which is deficient in the gene PTEN.

In another embodiment the cancer is in a metastatic state, and more particularly the cancer produces metastases to the bone.

In one embodiment of the invention, particularly the cancer is in a metastatic state, and more particularly the cancer produces skin metastases.

In one embodiment of the invention, particularly the cancer is in a metastatic state, and more particularly the cancer produces lymphatic metastases.

In one embodiment of the invention, the cancer is in a non-metastatic state.

The compositions of the invention may be obtained by conventional procedures using conventional pharmaceutical excipients, well known in the art. Thus, compositions intended for oral use may contain, for example, one or more colouring, sweetening, flavouring and/or preservative agents.

A compound such as Compound I may normally be administered to a warm-blooded animal at a unit dose within the range 5-5000 mg/m$^2$ body area of the animal, i.e. approximately 0.1-200 mg/kg, and this normally provides a therapeutically-effective dose. A unit dose form such as a tablet or capsule will usually contain, for example 1-250 mg of active ingredient. Preferably a unit dose form such as a tablet or capsule will usually contain, for example 10-70 mg of active ingredient. Preferably a daily dose in the range of 10-150 mg/kg is employed, for example 10-50 mg/kg administered twice daily. However the daily dose will necessarily be varied depending upon the host treated, the particular route of administration, and the severity of the illness being treated. Accordingly the practitioner who is treating any particular patient may determine the optimum dosage. For example, a pharmaceutical composition of the present invention suitable for oral administration could comprise 1-200 mg/mL of Compound I in 0.5% hydroxypropylmethylcellulose (HPMC).

A taxane (such as docetaxel) will normally be administered to a warm-blooded animal at a unit dose known to the skilled practitioner as a therapeutically effective dose. For a single dosage form, the active ingredients may be compounded with an appropriate and convenient amount of excipients which may vary from about 5 to about 98 percent by weight of the total composition. Dosage unit forms will generally contain about 20 mg to about 500 mg of active ingredient. However the daily dose will necessarily be varied depending upon the host treated, the particular route of administration, and the severity of the illness being treated. Accordingly the optimum dosage may be determined by the practitioner who is treating any particular patient.

In any embodiment described herein, the taxane (for example docetaxel) may be dosed at 50-140 mg/m$^2$ body area of the animal on the day(s) when it is dosed, for example 60-120 mg/m$^2$ body area of the animal, or for example 65-110 mg/m$^2$ body area of the animal. In any embodiment described herein, the Compound [I] or a pharmaceutically acceptable salt thereof may be dosed at 10-50 mg/kg twice daily on days when it is dosed. The skilled person understands that if a pharmaceutically acceptable salt of Compound [I] is used, the Compound [I] content of the dose is less than 100% and the actual mass of the salt being dosed will be higher than the aforementioned 10-50 mg/kg twice daily, depending on the mass of the counterion used to make the particular salt, and the stoichiometry of the salt. The actual doses to be used for a given patient should be determined by an appropriately qualified physician.

The dosage of each of the drugs and their proportions have to be composed so that the best possible treatment effects, as defined by national and international guidelines (which are periodically reviewed and re-defined), will be met.

EXPERIMENTAL DETAILS

Compound [I] may be prepared according to the procedures described in WO2011/051704, relevant details of which are incorporated herein by reference.

Female Swiss athymic nu/nu mice were implanted subcutaneously in the left flank with 0.1 ml PC3 cells ($1 \times 10^6$ cells in Iscove's serum free medium mixed 50:50 with matrigel) or HCC70 cells ($1 \times 10^6$ cells in RPMI serum free medium mixed 50:50 with matrigel). Once tumours reached ~200-500 mm$^3$ in size animals were randomised into control and treatment groups.

Compound [I] in the free base form was dosed either in the presence or absence of ABT (aminobenzotriazole). For groups where ABT was administered, Compound [I] was formulated once weekly either alone in 10% DMSO/60% TEG/30% WFI or in the presence of ABT at 10 mg/ml. For twice daily dosing Compound [I] was co-dosed with ABT at hour 0, and then administered alone as the single formulation at hour 6-8. For groups where ABT was not administered, Compound [I] was formulated once weekly as a suspension in HPMC/Tween and dosed once or twice daily (0 and 6-8 hours)

Docetaxel (Taxotere™) was formulated fresh in physiological saline at 1.5 mg/ml and dosed as a single i.v. bolus at a rate of 0.1 ml/10 g on Day 0, 24 hours prior to the administration of Compound [I].

Tumour volume was calculated twice weekly from bilateral calliper measurements using the formula (length×width×width)×π/6. Growth inhibition from the start of treatment was assessed by comparison of the geometric mean change in tumour volume for the control and treated groups. Statistical significance was evaluated using a one-tailed "t"-test.

Figure 1:
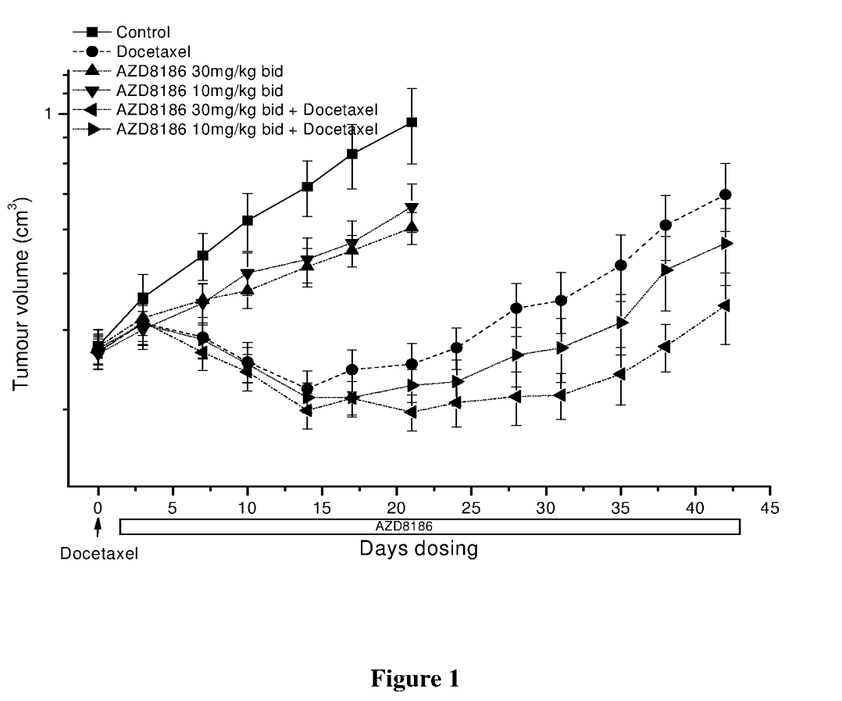
FIG. 1—Long Term Continuous Dosing of Compound [I] formulated with ABT in Combination With Docetaxel in a mouse PC3 Xenograft Model.

This figure shows the change in tumour volume in a mouse PC3 (a prostate cancer cell line) xenograft model over a 42-day period when treated with:
 i. Compound [I] alone at a dose of 10 mg/Kg bid;
 ii. Compound [I] alone at a dose of 30 mg/Kg bid;
 iii. A taxane (docetaxel) alone;
 iv. A combination of Compound [I] at a dose of 10 mg/Kg bid and a taxane (docetaxel) together; and
 v. A combination of Compound [I] at a dose of 30 mg/Kg bid and a taxane (docetaxel) together.

FIG. 1 shows that use of the combination of Compound [I] and docetaxel appears to achieve additional tumour shrinkage when compared to the use of either Compound [I] or docetaxel alone.

Figure 2:
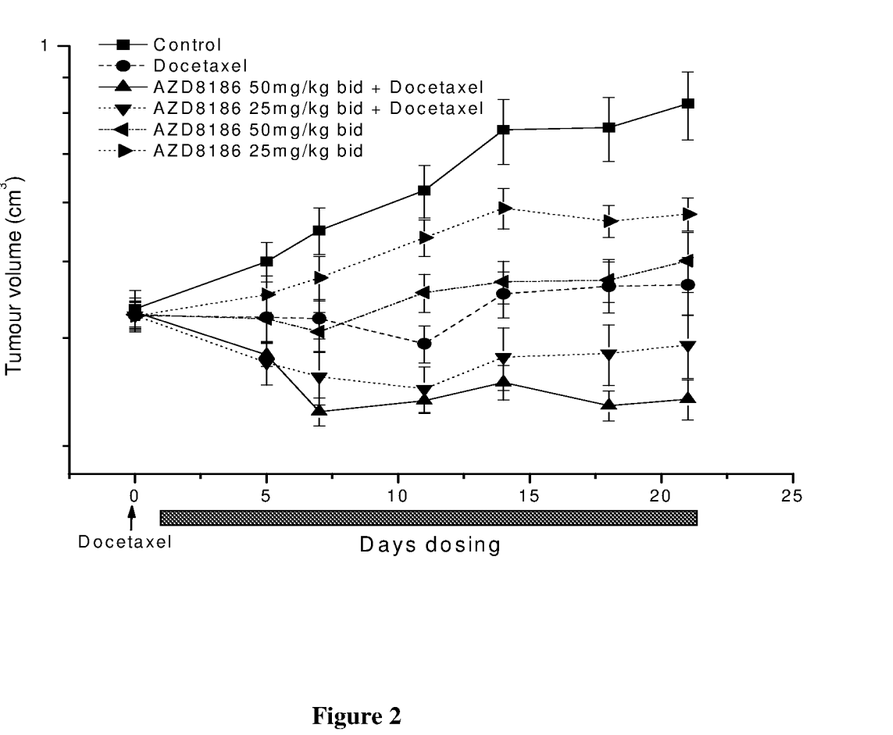
FIG. 2—Anti-tumour Activity of Compound [I] formulated in the Absence of ABT When Dosed Continually in Combination With Docetaxel in a mouse HCC70 Xenograft Model.

This figure shows the change in tumour volume in a mouse HCC70 (a breast cancer cell line) xenograft model over a 21-day period when treated with:
 i. Compound [I] alone at a dose of 25 mg/Kg bid;
 ii. Compound [I] alone at a dose of 50 mg/Kg bid;
 iii. A taxane (docetaxel) alone;
 iv. A combination of Compound [I] at a dose of 25 mg/Kg bid and a taxane (docetaxel) together; and
 v. A combination of Compound [I] at a dose of 50 mg/Kg bid and a taxane (docetaxel) together.

FIG. 2 again shows that use of the combination treatment appears to achieve additional tumour shrinkage over the use of either Compound [I] or docetaxel alone.

Figure 3:
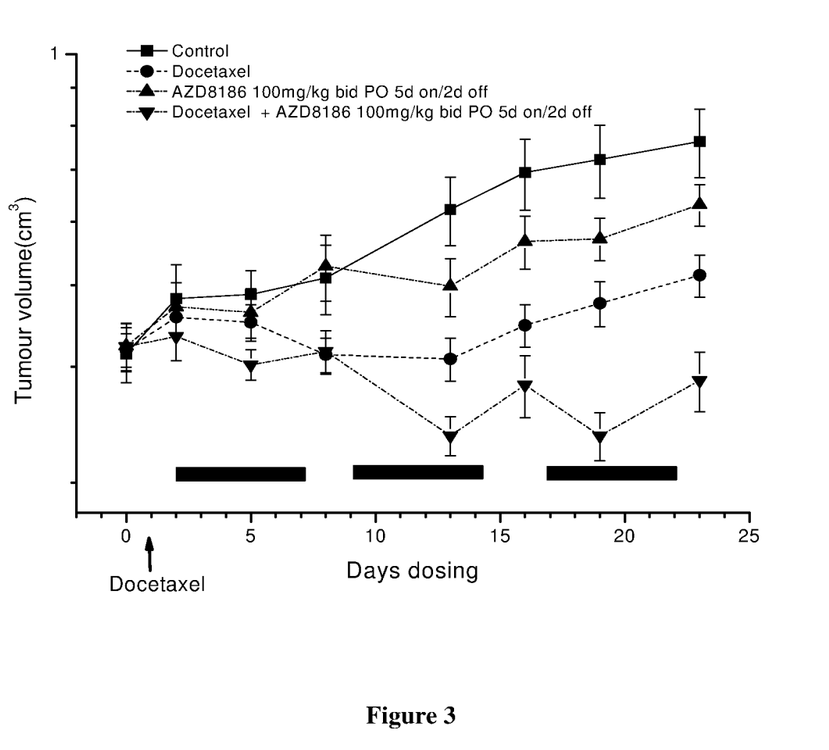
FIG. 3—Anti-tumour Activity of Intermittent High Dose Compound [I] formulated in the absence of ABT when dosed in combination with Docetaxel in an HCC70 Xenograft Model.

FIG. 3 shows the change in tumour volume in a mouse HCC70 (a breast cancer cell line) xenograft model over a 23-day period when treated with:
 i. A taxane (docetaxel) alone;
 ii. Compound [I] alone at a dose of 100 mg/Kg bid, wherein the Compound [I] was administered on 5 consecutive days of a 7 day period only, with no agent administered on the remaining 2 days; and
 iii. A combination of Compound [I] at a dose of 100 mg/Kg bid and docetaxel together, wherein the Compound [I] was administered on 5 consecutive days of a 7 day period only, with no agent administered on the remaining 2 days.

FIG. 3 shows that even intermittent dosage of Compound [I] in combination with a single dose of docetaxel can result in sustained additional anti-tumour activity over either docetaxel or Compound [I] alone.

Figure 4:
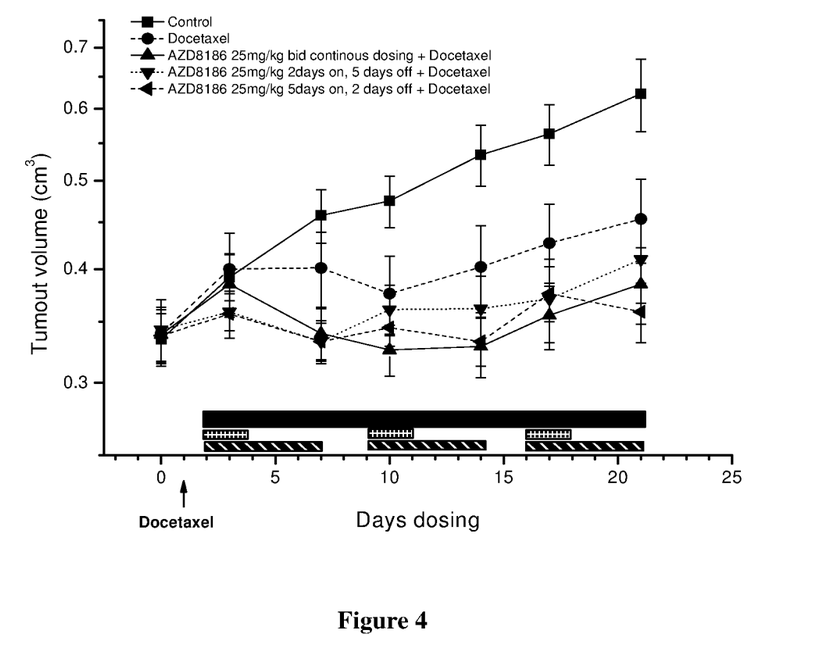
FIG. 4—Anti-tumour Activity of Intermittent Low Dose Compound [I] formulated in the absence of ABT when dosed in combination with Docetaxel in an HCC70 Xenograft Model.

This figure shows the change in tumour volume in a mouse HCC70 (a breast cancer cell line) xenograft model over a 21-day period when treated with:
 i. A taxane (docetaxel) alone;
 ii. A combination of Compound [I] at a dose of 25 mg/Kg bid and a taxane (docetaxel) together, continuously dosed;
 iii. A combination of Compound [I] at a dose of 25 mg/Kg bid and docetaxel together, wherein the Compound [I] was administered on 5 consecutive days of a 7 day period only, with no agent administered on the remaining 2 days.
 iv. A combination of Compound [I] at a dose of 25 mg/Kg bid and docetaxel together, wherein the Compound [I] was administered on 2 consecutive days of a 7 day period only, with no agent administered on the remaining 5 days.

FIG. 4 shows that even intermittent dosage of Compound [I] at a relatively low dose in combination with a single dose of docetaxel can result in sustained additional anti-tumour activity when compared to either docetaxel or Compound [I] alone.

The invention claimed is:
1. A method of treating cancer in a warm-blooded animal comprising administering to said animal an effective amount of Compound [I], or a pharmaceutically acceptable salt thereof:

Compound [I]

in combination with an effective amount of a taxane, wherein Compound [I], or a pharmaceutically acceptable salt thereof, is dosed intermittently.

2. The method of claim 1, wherein the taxane is docetaxel.

3. The method of claim 1, wherein Compound [I], or a pharmaceutically acceptable salt thereof, and the taxane are administered in a dosage cycle of 8-29 days in length.

4. The method of claim 3, wherein the taxane is administered only once in a given dosage cycle.

5. The method of claim 4, wherein the taxane is administered within the 24 hours prior to the first administration of Compound [I], or a pharmaceutically acceptable salt thereof, in a given dosage cycle.

6. The method of claim 3, wherein the dosage cycle is 15-29 days long and comprises administration of the taxane within 24 hours prior to the first administration of Compound [I], or a pharmaceutically acceptable salt thereof, followed by intermittent dosing of Compound [I], or a pharmaceutically acceptable salt thereof, in 7 day periods consisting of 5 days wherein Compound [I], or a pharmaceutically acceptable salt thereof, is dosed followed by 2 days wherein no Compound [I], or a pharmaceutically acceptable salt thereof, is dosed.

7. The method of claim 3, wherein the dosage cycle is 15-29 days long and comprises administration of the taxane within 24 hours prior to the first administration of Compound [I], or a pharmaceutically acceptable salt thereof, followed by intermittent dosing of Compound [I], or a pharmaceutically acceptable salt thereof in 7 day periods consisting of 4 days wherein Compound [I], or a pharmaceutically acceptable salt thereof, is dosed followed by 3 days wherein no Compound [I], or a pharmaceutically acceptable salt thereof, is dosed.

8. The method of claim 1, wherein the taxane is dosed at 50-140 mg/m$^2$ of patient surface area on the day(s) when it is dosed and Compound [I], or a pharmaceutically acceptable salt thereof, is dosed at 0.1-200 mg/kg twice daily on the days when it is dosed.

9. The method of claim 1, wherein the cancer is selected from castrate-resistant prostate cancer, squamous non-small cell lung cancer, colorectal cancer, pancreatic cancer and triple negative breast cancer.

10. The method of claim 3, wherein Compound [I] or a pharmaceutically acceptable salt thereof is not administered for 1, 2, 3, 4, 5, 6 or 7 days within a given dosage cycle.

11. The method of claim 3, wherein the dosage cycle is 8 days long and comprises administering Compound [I] or a pharmaceutically acceptable salt thereof for 5 consecutive days followed by 2 consecutive days in which Compound [I] or a pharmaceutically acceptable salt thereof is not administered.

12. The method of claim 3, wherein the dosage cycle is 8 days long and comprises administering Compound [I] or a pharmaceutically acceptable salt thereof for 4 consecutive days followed by 3 consecutive days in which Compound [I] or a pharmaceutically acceptable salt thereof is not administered.

13. The method of claim 3, wherein the dosage cycle is 8 days long and comprises administering Compound [I] or a pharmaceutically acceptable salt thereof for 3 consecutive days followed by 4 consecutive days in which Compound [I] or a pharmaceutically acceptable salt thereof is not administered.

* * * * *